US012702520B2

(12) United States Patent
Eftekari et al.

(10) Patent No.: US 12,702,520 B2
(45) Date of Patent: Aug. 11, 2026

(54) LOW-COSTS SURGICAL MICROSCOPE

(71) Applicant: Wisconsin Alumni Research Foundation, Madison, WI (US)

(72) Inventors: Sahand Eftekari, Madison, WI (US); Ellen Shaffrey, Madison, WI (US); Samuel Poore, Madison, WI (US); Weifeng Zeng, Middleton, WI (US); Aaron Dingle, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 316 days.

(21) Appl. No.: 18/527,905

(22) Filed: Dec. 4, 2023

(65) Prior Publication Data

US 2025/0177083 A1 Jun. 5, 2025

(51) Int. Cl.
*G02B 21/00* (2006.01)
*A61B 90/25* (2016.01)

(52) U.S. Cl.
CPC .......... *A61B 90/25* (2016.02); *G02B 21/0012* (2013.01)

(58) Field of Classification Search
CPC .... A61B 90/25; A61B 90/20; G02B 21/0012; G02B 21/20; G02B 21/22; G02B 21/368; G02B 23/18
See application file for complete search history.

(56) References Cited

U.S. PATENT DOCUMENTS

| | | | | |
|---|---|---|---|---|
| 4,763,968 | A * | 8/1988 | Minami | G02B 21/22 359/377 |
| 6,320,696 | B1 * | 11/2001 | Greenberg | G02B 21/22 359/377 |
| 7,242,522 | B2 * | 7/2007 | Kanai | G02B 25/004 359/415 |
| 7,564,620 | B2 * | 7/2009 | Winterot | G02B 27/0075 359/744 |
| 7,768,701 | B2 * | 8/2010 | Namii | A61B 90/36 359/377 |
| 9,823,457 | B2 * | 11/2017 | Li | G02B 21/367 |
| 10,859,810 | B2 * | 12/2020 | Hewlett | G02B 27/028 |
| 2004/0120031 | A1 * | 6/2004 | Fukaya | G02B 21/0012 359/375 |
| 2005/0063058 | A1 * | 3/2005 | Langley | G02B 27/0006 359/819 |
| 2010/0103247 | A1 * | 4/2010 | Lim | A61B 90/36 348/47 |
| 2012/0087006 | A1 * | 4/2012 | Signaigo | G02B 21/0012 359/813 |

* cited by examiner

*Primary Examiner* — Mustak Choudhury
(74) *Attorney, Agent, or Firm* — Boyle Fredrickson, S.C.

(57) ABSTRACT

A robust and low-cost surgical microscope is created by incorporating commercial binoculars intended for close focusing into a housing having a contained mirror system providing both a diversion of the optical path and a reduced distance between the microscope and surgical site thus adapting these binoculars for ergonomic surgical application.

17 Claims, 2 Drawing Sheets

LOW-COSTS SURGICAL MICROSCOPE

BACKGROUND OF THE INVENTION

The present invention relates to stereoscopic microscopes for use in surgery and, in particular, to robust low-cost stereoscopic microscopes for use in training and in underdeveloped countries.

Microsurgical techniques allow reattachment of nerves, small blood, and lymphatic vessels and permit re-plantation, for example, of severed fingers and free tissue transfer which moves tissue from one part of the body to another for patient reconstruction.

Such techniques use specialized microscopes adapted for surgical use, the microscopes and typically providing stereoscopic optics for good depth perception, a magnification range from 4× to 40×, and an eyepiece angulation and focal distance allowing ergonomic positioning of the surgeon's eyes and hands.

Microscopes for this purpose can cost many thousands of dollars and may require careful maintenance. Both of these factors limit the availability of these microscopes both for training necessary to master microsurgical techniques and for use in regions of the world where it can be difficult to service these precision devices.

SUMMARY OF THE INVENTION

The present inventors have recognized that off-the-shelf binoculars, for example, binoculars designed with close focus and intended for viewing of butterflies and the like, can be leveraged to produce a low-cost and robust surgical microscope suitable for both training and the clinical practice of microsurgery, particularly in remote locations where it is difficult to service or obtain precision equipment. A specially designed housing holds the binocular optics aligned with a set of planar mirrors that operate to adapt the eyepiece angle and the focal length of the binoculars for an ergonomic use in surgery. In one embodiment, a simple table clamp supports the housing and optics at an appropriate height.

More specifically, the invention can provide a microscope system having a binocular assembly including left and right eyepieces and corresponding left and right objective lenses separated by optical-path-folding left and right prism assemblies, the objective lenses receiving light along the left and right axes. A mirror assembly of at least two planar mirrors is positioned along an optical path between the objective lenses and a corresponding focal spot at an operating site, the planar mirrors cooperating with the binocular assembly to divert the angle of light received from the operating site to align with the left and right axes of the objective lenses.

It is thus a feature of at least one embodiment of the invention to employ the economies of scale available with binocular optics to produce a low-cost surgical microscope.

The mirrors may operate to provide an acute angle of light diversion.

It is thus a feature of at least one embodiment of the invention to provide the desired angled optical path downstream from the objective lenses to avoid the need for complex prism assemblies or the like.

The angle of diversion may be 45° plus or minus 5°

It is thus a feature of at least one embodiment of the invention to permit an ergonomic and comfortable viewing angle by the physician.

The binocular optics may include a focusing mechanism for changing a focal length of the binocular assembly and changing the relative separation between at the eyepieces and/or between the objective lenses.

It is thus a feature of at least one embodiment of the invention to provide binocular optics suitable for close focus where parallax becomes an issue.

The individual planar mirrors may divert the light from both the left and right axes.

It is thus a feature of at least one embodiment of the invention to share optics between the left and right eye for reduced cost and complexity.

The at least two mirrors may be rear-surface mirrors.

It is thus a feature of at least one embodiment of the invention to permit the use of low-cost mirrors that are naturally resistant to environmental contamination.

The microscope may include a housing providing a first receptacle for removably receiving a commercial off-the-shelf pair of binoculars providing the binocular assembly, the housing also providing a support for the first and second mirrors.

It is thus a feature of at least one embodiment of the invention to allow use of mass-produced and thus low-cost commercial binoculars with minimal or no modification.

The receptacle may include at least one stop for positively orienting the pair of binoculars to a predetermined optical axis with respect to the housing.

It is thus a feature of at least one embodiment of the invention to allow ready repair of the principal optical components of the device simply by replacing the binocular element.

The microscope system may further include a housing support arm adapted to attach to a table supporting a patient and to attach to the housing to suspend the housing above the operating site on the patient at a focal distance of the microscope.

It is thus a feature of at least one embodiment of the invention to reduce the cost of the microscope support structure by taking advantage of the rigid structure offered by a patient table or the like.

The microscope system may include a receptacle for receiving a cell phone having a camera and orienting the camera with respect to the housing for capturing an image of the operating site.

It is thus a feature of at least one embodiment of the invention to provide a similar leveraging of cell phone technology to provide recording and video streaming capabilities.

These particular objects and advantages may apply to only some embodiments falling within the claims and thus do not define the scope of the invention.

BRIEF DESCRIPTION OF THE DRAWINGS

FIG. 1 is a partially exploded, perspective view of a surgical microscope constructed according to the present invention, as supported by an arm attached to a patient table above an operating site, and showing insertion of a commercial off-the-shelf pair of binoculars into a housing of the microscope and a positioning of a standard cell phone in a pocket on the housing for video streaming or the like;

FIG. 2 is an elevational side cross-sectional view of the surgical microscope of FIG. 1 showing the internal optical path through the internal optics of two pairs of binoculars inserted into the housing and the mirrors contained in the housing.

DETAILED DESCRIPTION OF THE PREFERRED EMBODIMENT

Figures 1, 2:
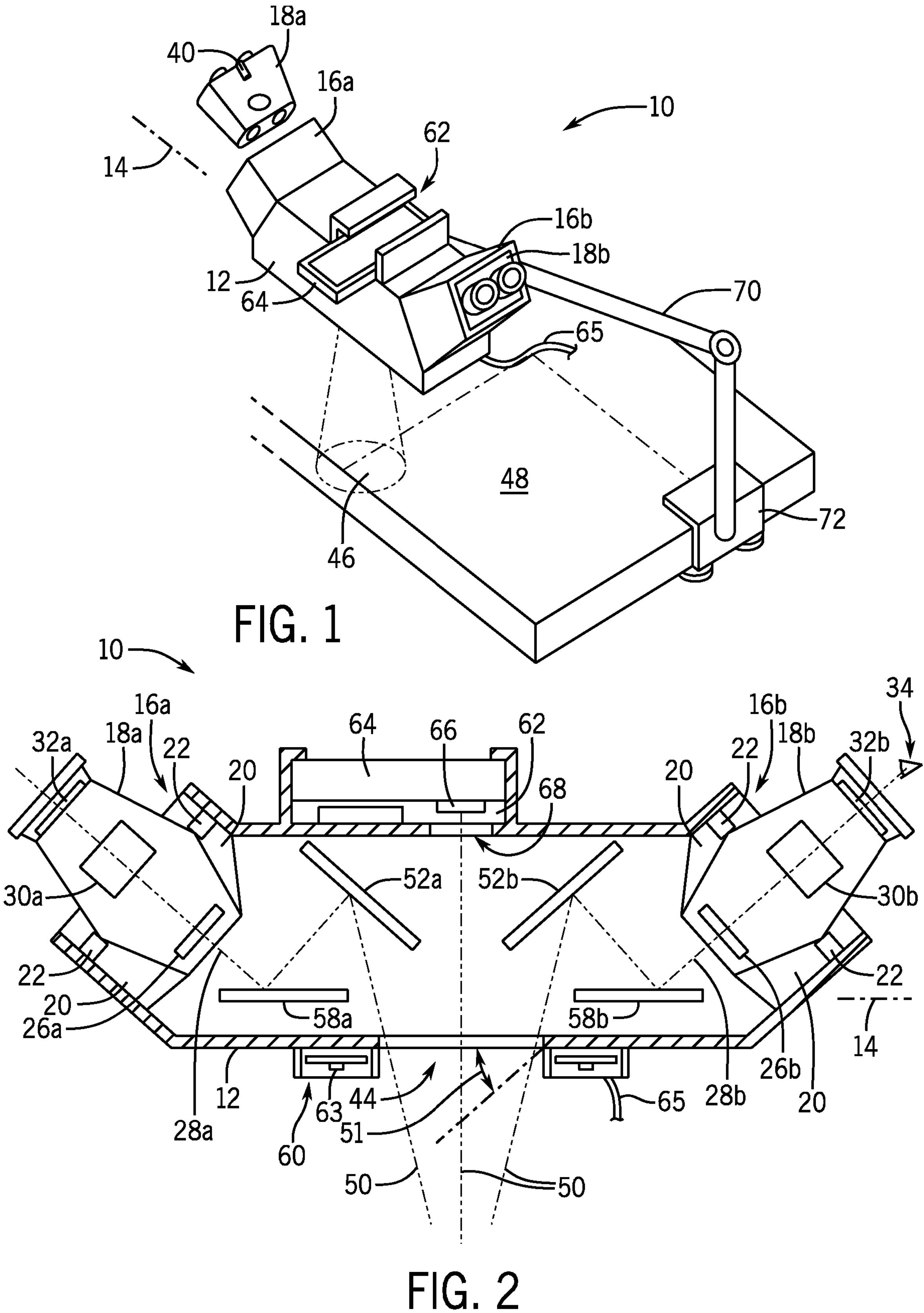

Referring now to FIGS. 1 and 2, a low-cost surgical microscope 10 of the present invention may include a housing 12 extending along a horizontal axis 14 between receptacles 16*a* and 16*b* positioned at the axial ends of the housing 12 and providing passageways into an interior volume of the housing 12. The receptacles 16 may open upwardly, for example, by about 45° with respect to the axis 14 and provide respective sockets for receiving commercial off-the-shelf (COTS) binoculars 18*a* and 18*b* therein.

As so received, each of the binoculars 18 are registered with respect to angle and insertion depth with the housing 12 by stop members 20 matching to the outer housing of the binoculars 18 being used. The binoculars 18 are held in the sockets of the receptacles 16 against ready dislodgment by elastomeric gaskets 22 that are sufficiently compliant to allow removal of the binoculars 18 as required.

As best seen in FIG. 2, the binoculars 18*a* and 18*b* are received within the receptacles 16 so that their objective lenses 26*a* and 26*b* face into the housing 12 and eyepieces 32*a* and 32*b* extend out from the housing 12 at a comfortable working angle for a surgeon using the device at about 45° from the horizontal axis 14. As so positioned, the objective lenses 26*a* and 26*b* receive light along first axes 28*a* and 28*b* generally matching the angle of the eyepieces 32 of approximately 45° from the horizontal axis 14 or other comfortable working angle.

The binoculars 18 will typically include an optical-path-folding element 30*a* and 30*b* such as a Porro prism positioned between each eyepiece 32 and its respective objective lens 26. Binoculars 18 suitable for use with the present invention are commercially available from a number of sources including from Ricoh Imaging Americas Corporation under the trade name Papilio II having a magnification of 6.5 and an objective diameter of 21 mm or magnification of 8.5 and an objective diameter of 21 mm with an exit pupil of 3.2 mm or 2.5 mm, respectively. Such commercial binoculars may provide an eye relief of 15 mm and a focusing range from 1.6 feet to infinity and are currently available for less than $150.

Significantly, and for this purpose, the binoculars 18 may provide "close-focus," for example, useful in observing insects, and for this purpose will include a linkage between eyepiece and objective lens separation for focusing and lateral eyepiece spacing, or objective lens spacing for parallax correction, available in the above cited binocular product under the trade name of Convergent Lens Optical System Engineering. In this regard, the binoculars 18 includes a focus knob 40 (shown in FIG. 1) that may be turned to change the focus parallax adjustment simultaneously. The binoculars 18 may further provide a separate diopter adjustment for correcting for differences in eyesight focus of a user's left and right eye. Consistent for their intended commercial use in the field, such binoculars may be robust and extremely lightweight, for example, less than 11 ounces.

Referring still to FIG. 2, a bottom surface of the housing 12 may provide for an opening 44 for receiving light from an operating site 46 above a table surface 48 at a focus range of the binoculars 18 (as modified by the optical path within the housing to be described). The opening 44 admits light traveling generally along a vertical axis 50, for example, perpendicular to axis 14 within a range of plus or minus 10° or plus or minus 5°.

The upwardly traveling light along axis 50 may be received by planar rear surface mirrors 52*a* and 52*b* facing downward and positioned near the upper surface of the housing 12 within the housing volume. These mirrors 52*a* and 52*b* direct the received light by reflection downward and leftward or rightward, respectively, toward corresponding planar rear surface mirrors 58*a* and 58*b* facing upwardly and positioned near the bottom of the housing 12. The mirrors 58*a* and 58*b* are oriented to direct the received light from the mirrors 52*a* and 52*b* toward the objective lenses 26 of the left and right binoculars 18 along axes 28*a* and 28*b*, respectively.

The net effect of the mirrors 52 and 58 is to fold the optical path between the operating site 46 and the binoculars 18 allowing closer positioning of the binoculars 18 to the operating site 46. Further, the mirrors 52 and 58 provide an offset angle between axes 28 and axes 50 to provide improved ergonomic function of the microscope, allowing the user to comfortably look downward from horizontal at angle 51 at about 45° with respect to axis 14 while providing a substantially vertical viewing of the operating site 46, thus effecting an angular diversion of approximately 45° plus or minus 5°. This arrangement also allows two operating micro-surgeons to have the same vantage as one another, directly looking downward at the microsurgical field.

As noted, the mirror array provides the proper vantage for the operating microsurgeon but also provides the proper focal length. Each mirror further rotates the image 180 degrees such that the final image into the eye is a 360 degree rotation of the original image, imperceivable to the operating surgeon.

A bottom of the housing 12 may support an LED light ring 60 having internal LEDs 63 directing light downward for shadow-less illumination of the operating site 46 and surrounding the opening 44. The LED light ring 60 may receive power from a remote wall transformer or the like through cord 65.

Referring to FIGS. 1 and 2, an upper surface of the housing 12 may optionally include a pocket 62 for retaining and aligning a commercial off-the-shelf cell phone 64 of a type having an internal camera, so that a camera lens 66 is positioned to receive light through the opening 44 to image the operating site 46. In one embodiment, the camera lens 66 is positioned centered above the opening 44 to receive light through a second opening 68 in an upper wall of the housing 12 aligned with opening 44 along axis 50. This light may be received between mirrors 52*a* and 52*b* of the interior of the housing 12.

The inventors contemplate that alternative positions of the cell phone 64 may be used and that light received by the cell phone camera lens 66 may be conducted by additional mirrors or the like. Incorporation of a cell phone 64 allows images of the operating site 46 to be recorded and streamed, again leveraging capabilities of mass-market products to provide a surgical stereo microscope at reduced cost.

Referring again to FIG. 1, in some embodiments, the housing 12 may be supported above the table surface 48 by an articulated arm 70 that may be clamped by clamp member 72 to a table edge, for example, of an operating table or the like. The articulated arm 70 operates to support the housing 12 generally with the axis 14 horizontal above the operating site 46 at a proper elevation for focusing. Minor focus adjustments may then be implemented with the focus knob 40 on the binoculars 18 themselves. In this way expensive support mechanisms can be avoided taking advantage of the existing structure of the table or the like.

Figure 3:
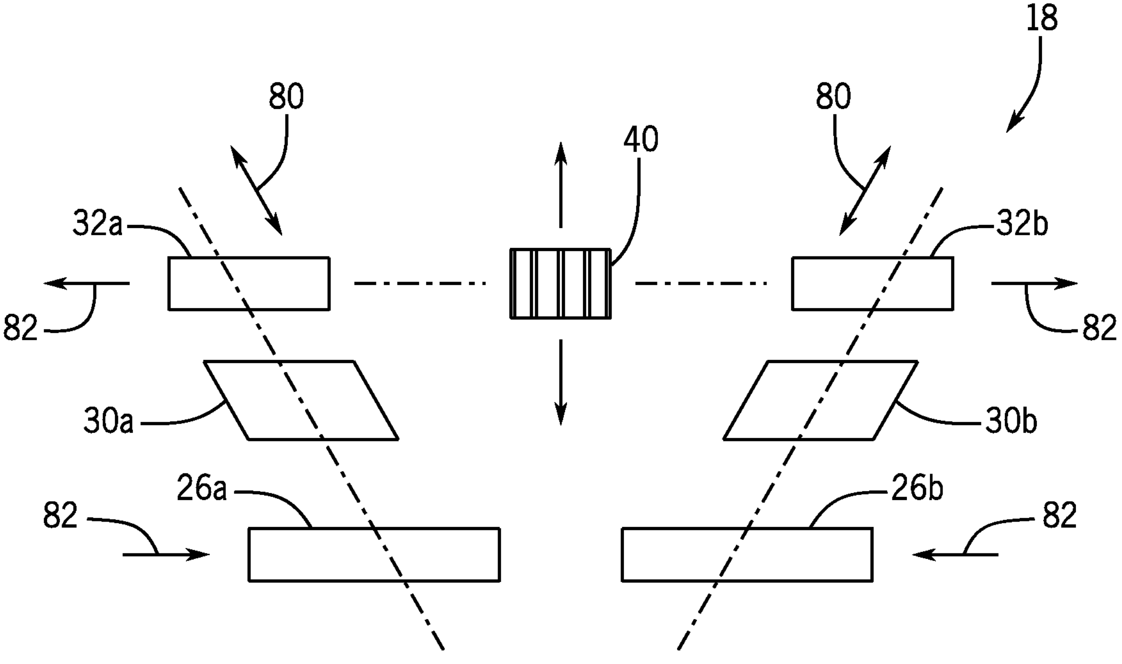
FIG. 3 is a simplified diagram of the eyepiece and objective lenses of an individual binocular showing a tandem changing of lenses' separation between pairs of eyepieces or pairs of objective lenses for parallax correction and separation between individual eyepieces and respective objective lenses for focusing, both required for close focus.

Referring now to FIG. 3, as noted, the binoculars 18 are desirably configured for close focusing and thus may include a focus knob 40 operating to change the relative spacing between the eyepieces 32*a* and 32*b* and their corresponding objective lenses 26*a* and 26 indicated by arrows 80 (providing standard focus correction) while also changing the relative spacing between one or both of the pairs of eyepieces 32*a* and 32*b* and the objective lenses 26 indicated by arrows 82, thus accommodating parallax effects associated with close focus work suitable for surgical application.

It is noted that the various lenses described herein including the objective lenses 26 and eyepieces 32 will generally be compound lenses and other lens elements may be incorporated into the binoculars' 18 field correction and chromatic adjustment and the like as is generally understood in the art. It will be understood that the axes described with respect to the optical path represent centerlines of cones of light passing from the operating site 46 to the user's eyes 34.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A microscope system comprising:

a binocular assembly including left and right eyepieces and corresponding left and right objective lenses separated by optical-path-folding left and right prism assemblies, the objective lenses receiving light along left and right axes; and a mirror assembly of at least two planar mirrors positioned along an optical path between the objective lenses and a corresponding focal spot at an operating site, the at least two planar mirrors operating with the binocular assembly to divert the angle of light received from the operating site to align with the left and right axes of the objective lenses.

2. The microscope system of claim 1 wherein at least two mirrors operate to provide an acute angle of light diversion.

3. The microscope system of claim 2 wherein the angle of diversion is 45° plus or minus 5°.

4. The microscope system of claim 1 including a focusing mechanism in the binocular assembly for changing a focal length of the binocular assembly and wherein the focusing mechanism further changes the relative separation between the eyepieces and/or between the objective lenses.

5. The microscope system of claim 1 wherein individual planar mirrors of the at least two mirrors of the mirror assembly divert the light from both the left and right axes.

6. The microscope system of claim 1 wherein the at least two mirrors are rear surface mirrors.

7. The microscope system of claim 1 wherein including a housing providing a first receptacle for removably receiving a commercial off-the-shelf pair of binoculars providing the binocular assembly, the housing also providing a support for the first and second mirrors.

8. The microscope system of claim 7 wherein the receptacle includes at least one stop for positively orienting the pair of binoculars to a predetermined optical axis with respect to the housing.

9. The microscope system of claim 7 wherein providing a housing support arm including adapted to attach to a table supporting a patient and to attach to the housing to suspend the housing above the operating site on the patient at a focal distance of the microscope.

10. The microscope system of claim 7 wherein including a receptacle for receiving a cell phone having a camera and orienting the camera with respect to the housing for capturing an image of the operating site.

11. A microscope system comprising:

a binocular assembly including left and right eyepieces and corresponding left and right objective lenses separated by optical-path-folding left and right prism assemblies, the objective lenses receiving light along left and right axes; and a mirror assembly of at least two planar mirrors positioned along an optical path between the objective lenses and a corresponding focal spot at an operating site, the at least two planar mirrors operating with the binocular assembly to divert the angle of light received from the operating site to align with the left and right axes of the objective lenses;

further including a second binocular assembly including left and right eyepieces and corresponding left and right objective lenses separated by optical-path-folding left and right prism assemblies, the left and right objective lenses receiving light along second left and right axes;

further including a second mirror assembly of at least two planar mirrors positioned along an optical path between the objective lenses and corresponding focal spots at an operating site, the first and second planar mirrors cooperating with the second binocular assembly to divert the angle of light received from the operating site to align with the second left and right axes.

12. A binocular adapter system comprising:

a housing providing a receptacle for receiving a pair of commercial off-the-shelf binoculars providing a binocular assembly including left and right eyepieces and corresponding left and right objective lenses separated by optical-path-folding left and right prism assemblies, the objective lenses receiving light along left and right axes, the receptacle including at least one stop for positively orienting the pair of binoculars to a predetermined optical axis;

wherein the housing further supports a mirror assembly of at least two planar mirrors positioned along an optical path between the objective lenses and corresponding focal spots at an operating site, the first and second planar mirrors cooperating with the binocular assembly to divert the angle of light received from the operating site to align with the left and right axes by an acute angle.

13. The microscope system of claim 12 wherein individual planar mirrors of the mirror assembly divert the light from both the left and right axes.

14. The microscope system of claim 12 wherein the mirrors are rear surface mirrors.

15. The microscope system of claim 12 further including a housing support adapted to attach to a table supporting a patient to suspend the housing above the operating site on the patient at a focal distance of the microscope.

16. The microscope system of claim 12 wherein including a receptacle for receiving a cell phone having a camera and orienting the camera with respect to the housing for capturing an image of the operating site.

17. A binocular adapter system comprising:

a housing providing a receptacle for receiving a pair of commercial off-the-shelf binoculars providing a binocular assembly including left and right eyepieces and corresponding left and right objective lenses separated by optical-path-folding left and right prism assemblies, the objective lenses receiving light along left and right axes, the receptacle including at least one stop for positively orienting the pair of binoculars to a predetermined optical axis;

wherein the housing further supports a mirror assembly of at least two planar mirrors positioned along an optical path between the objective lenses and corresponding focal spots at an operating site, the first and second planar mirrors cooperating with the binocular assembly to divert the angle of light received from the operating site to align with the left and right axes by an acute angle;

wherein the housing further includes a second receptacle for receiving a second pair of commercial off-the-shelf binoculars providing a binocular assembly including left and right eyepieces and corresponding left and right objective lenses separated by optical-path-folding left and right prism assemblies, the objective lenses receiving light along left and right axes, the receptacle including at least one stop for positively orienting the pair of binoculars to a predetermined optical axis; and wherein the housing further supports a mirror assembly of at least two planar mirrors positioned along an optical path between the objective lenses of the second pair and corresponding focal spots at an operating site, the first and second planar mirrors of the second pair cooperating with the binocular assembly to divert the angle of light received from the operating site to align with the left and right axes by an acute angle.

* * * * *